United States Patent [19]

Kaletta et al.

[11] Patent Number: 5,162,518

[45] Date of Patent: Nov. 10, 1992

[54] HETEROCYCLIC COMPOUNDS AND PORPHYRIN COMPOUNDS OBTAINABLE THEREFROM

[75] Inventors: Bernd Kaletta, Leverkusen, Fed. Rep. of Germany; Meinhard Rolf, Charlston, S.C.; Walther Wolf, Bischofsmais, Fed. Rep. of Germany; David R. Terrell, Lint, Belgium

[73] Assignee: Bayer Aktiengesellschaft, Leverkusen, Fed. Rep. of Germany

[21] Appl. No.: 824,762

[22] Filed: Jan. 17, 1992

Related U.S. Application Data

[63] Continuation of Ser. No. 600,033, Oct. 16, 1990, abandoned.

[30] Foreign Application Priority Data

Nov. 13, 1989 [DE] Fed. Rep. of Germany ....... 3937716

[51] Int. Cl.$^5$ ................ C07D 487/22; C07D 209/44; C07D 209/62; G03G 5/06
[52] U.S. Cl. .................................... 540/121; 548/471; 524/88
[58] Field of Search ......................................... 540/121

[56] References Cited

U.S. PATENT DOCUMENTS

| | | | |
|---|---|---|---|
| 3,657,272 | 4/1972 | Brach et al. | 260/314.5 |
| 3,723,421 | 3/1973 | Diana | 548/471 |
| 4,022,770 | 5/1977 | L'Eplattenier | 548/471 |
| 4,051,099 | 9/1977 | von der Crone | 548/471 |

FOREIGN PATENT DOCUMENTS

| | | |
|---|---|---|
| 0428214 | 5/1991 | European Pat. Off. . |
| 1169901 | 11/1969 | United Kingdom . |

OTHER PUBLICATIONS

Journal of the Chemical Society, 1939, pp. 1809–1820, The Chemical Society, Letchworth, GB P.A. Barrett et al.
"Justus Liebigs Annalen Der Chemie" vol. 529, 1937, pp. 205–211 Weinheim, DE J. H. Helberger.
Journal of the Chemical Society, 1940, pp. 1079–1092, The Chemical Society, Letchword, GB: P. A. Barrett et al.

*Primary Examiner*—Mark L. Berch

*Attorney, Agent, or Firm*—Sprung, Horn, Kramer & Woods

[57] ABSTRACT

Porphyrins of the formula

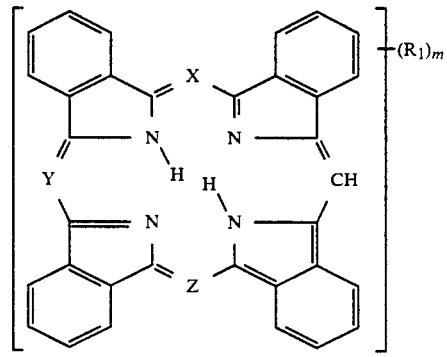

in which the substituents have the meaning given in the description are obtained by heating compounds of the formula

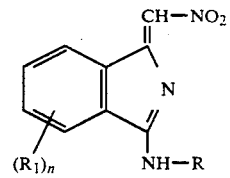

if appropriate in the presence of compounds of the formula

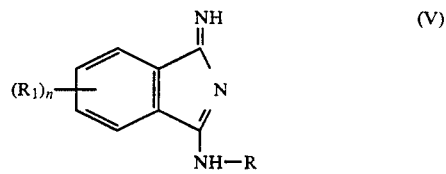

The porphyrins are used as pigments.

4 Claims, No Drawings

HETEROCYCLIC COMPOUNDS AND PORPHYRIN COMPOUNDS OBTAINABLE THEREFROM

This application is a continuation of application Ser. No. 600,033, filed Oct. 16, 1990.ABN.

The present invention relates to compounds of the formula

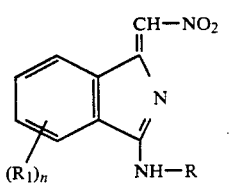

in which
R is H or a substituent
$R_1$ is a substituent
n is 0 to 2 and to a process for their preparation, characterized in that compounds of the formula

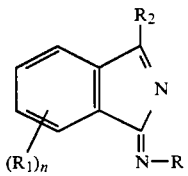

in which
$R_2$ is halogen, alkoxy or NHR
are reacted with nitromethane (III).

The substituents $R_1$ can be identical or different.

Examples of suitable substituents R are alkyl, aryl, hetaryl, acyl.

Examples of suitable substituents $R_1$ are R, alkoxy, halogen, carboxyl, carboxamido, cyano, $NO_2$.

Two adjacent substituents R can also form a carbocyclic or heterocyclic ring or ring system together with the C atoms on the benzene ring linking them.

Alkyl preferably represents $C_1-C_6$-alkyl, such as $CH_3$, $C_2H_5$, n— and i—$C_3H_7$ and n—, i— and t—$C_4H_9$.

Aryl preferably represents those carbocyclic-aromatic radicals containing 1, 2, 3 or 4, in particular 1 or 2, rings, such as phenyl, diphenylyl and naphthyl.

Hetaryl preferably represents those heterocyclic-aromatic radicals containing 1, 2, 3 or 4, in particular 1 or 2, five-, six- or seven-membered rings, at least one of which contains 1, 2 or 3, preferably 1 or 2, heteroatoms from the series comprising O, N, S. Examples of heterocyclic-aromatic radicals are:

pyridyl, pyrimidyl, pyrazinyl, triazinyl, furanyl, pyrrolyl, thienyl, quinolyl, curarinyl, benzofuranyl, benzoimidazolyl, benzoxazolyl, dibenzofuranyl, benzothienyl, dibenzothienyl, indolyl, carbazolyl, pyrazolyl, imidazoiyl, oxazolyl, isooxazolyl, thiazoiyl, indazoiyl, benzothiazoiyl, pyridazinyl, cinnolyl, quinazolyl, quinoxaiyl, phthalazinyl, phthalazinedionyl, phthalimidyl, chromonyl, naphtholactamyl, benzopyridonyl, orthosulphobenzimidyl, maleimidyl, naphtharidinyl, benzimidazolonyl, benzoxazolonyl, benzothiazoionyl, benzothiazolinyl, quinazolonyl, pyrimidonyl, quinoxalonyl, phthalozonyl, dioxapyrimidinyl, pyridonyl, isoquinolonyl, isoquinolinyl, isothiazolyl, benzisoxazolyl, benziso- thiazolyl, indazolonyl, acridinyl, acridonyl, quinazolinedionyl, thinoxalinedionyl, benzoxazinedionyl, benzoxazinonyl and naphthalimidyl.

The aryl and hetaryl radicals can have customary substituents, for example F, Cl, Br, alkyl, alkoxy, substituted or unsubstituted amino, carboxyl, carboxylate, carboxamido, sulpho, sulphonamido, alkoxycarbonyl, sulphonylamino, alkylsulphonyl, acylamino, aminocarbonyloxy. Halogen represents F, Cl, Br, I. Alkoxy is preferably $C_1-C_6$-alkoxy. Acyl preferably represents alkyl-(preferably $C_1-C_4$-alkyl) or substituted or unsubstituted phenylcarbonyl.

Preferred compounds (I) are those where n is 0 and those where n is 1 and $R_1$ is phenyl or $OCH_3$, R in each case representing H, acetyl, benzoyl, furthermore those where n is 2, two radicals $R_1$ together with the C atoms linking them representing a benzene ring.

The reaction of (II) with (III) is preferably carried out in an inert diluent at temperatures of 20° to 150° C., if appropriate in the presence of inert gases.

Suitable diluents are in particular water-miscible organic solvents, such as alcohols or ethers thereof, for example ethanol, methanol, butanol, ethylene glycol mono-$C_1-C_4$-alkyl ether, carboxylic acids, such as acetic acid; dioxane, pyridine, cyclic amides, such as dimethylformamide.

Compounds (I) (the formula given is one of the possible tautomeric forms) are valuable intermediates for the preparation of pigments.

The invention also relates to a process for the preparation of porphyrins or mixtures of porphyrines of the formula

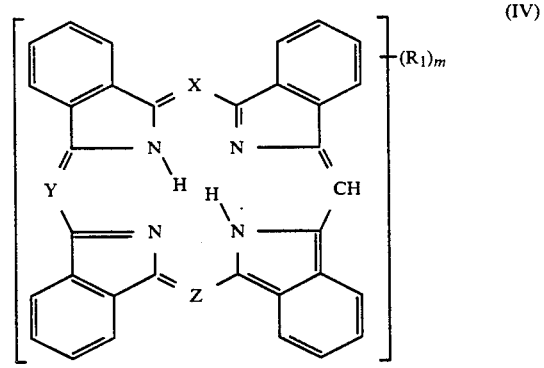

in which
X, Y, Z, independently of one another, denote CH or N, but at least one X, Y or Z represents N,
$R_1$ has the abovementioned meaning and
m is 0 to 8, characterized in that (I), if appropriate in a mixture with up to 20 mol of (V)

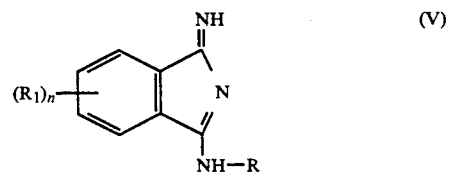

is heated to temperatures of 100° to 300° C., preferably 150° to 270° C.

The process yields uniform compounds (IV) or mixtures of different compounds (IV).

The reaction is preferably carried out in a solvent. Examples of suitable solvents are alcohols, such as pentanol, 2-methyl-2-butanol, 2-methyl-2-pentanol, 3-methyl-3-butanol, furthermore dipolar aprotic solvents, such as dimethylformamide, dimethylacetamide, dimethyl sulphoxide, N-methylpyrrolidone, and aliphatic or aromatic hydrocarbons, which can be unsubstituted or substituted by alkyl, alkoxy, halogen or nitro groups, such as decalin, xylene, metsitylene, chlorobenzene, dichlorobenzene, trichlorobenzene, naphthalene, 1-methylnaphthalene, 2-methylnaphthalene, 2-chloronaphthalene, 2-chloronaphthalene, and substituted or unsubstituted heterocyclic solvents, such as pyridine, picoline, quinoline.

The pigments of the type (IV) are obtained by the process described above in sufficient purity and can be used directly or after suitable formulation as pigments. Owing to their good pigment properties, pigments of the formula (IV) are suitable for a wide range of pigment applications and as organic photoconductors, for example for electrophotography.

Consequently, they can be used for the preparation of pigmented systems of very good fastness properties, such as mixtures with other substances, preparations, paints, printing inks, coloured paper and coloured macromolecular substances. A mixture with other substances can be understood to mean, for example, those containing inorganic white pigments, such as titanium dioxide (rutile). Examples are preparations of flush pastes containing organic liquids and, if appropriate, preservatives. The designation coating agent is understood to mean, for example, physically or oxidatively drying surface coatings, stoving enamels, reaction coatings, two-component coatings, emulsion paints for weather-resistant coatings and distempers. Printing inks are understood to mean those for paper, textile and metal sheet printing.

The novel pigments are in particular suitable for pigmenting macromolecular organic substances. The macromolecular substances can be of natural origin, such as rubber, can be obtained by chemical modification, such as acetylcellulose, cellulose butyrate or viscose, or produced synthetically, such as polymers, polyaddition products and polycondensation products. Examples are plastic materials, such as polyvinyl chloride, polyvinyl acetate, polyvinyl propionate, polyolefins, for example polyethylene or polyamides, super polyamides, polymers and copolymers made of acrylic esters or methacrylic esters, acrylonitrile, acrylamide, butadiene, styrene and polyurethanes and polycarbonates. The substances pigmented with the claimed products can be present in any desired form. Owing to their high weather fastness, the pigments of the formula (I) are particularly suitable for use in automotive paints, in particular for metallic effect paints.

The pigments of the formula (IV) have excellent water fastness, oil fastness, acid fastness, lime fastness, alkali fastness, solvent fastness, overcoating fastness, overspray fastness, sublimation fastness, heat fastness, vulcanizing fastness, give high yields, have good distribution in plastic materials and have in particular excellent light fastness and migration fastness.

Some of the compounds of the formula (IV) are known (for example (IV) where m is 0 and X, Y, Z are N). Accordingly, GB Patent 494,738 describes the following process: methylenephthalimidinoacetic acid is reacted in the presence of magnesium turnings in chloronaphthalene to give magnesium tetrabenzotriazaporphin. The magnesium tetrabenzotriazaporphin is dissolved in concentrated sulphuric acid and then poured into water to give a metal-free tetrabenzotriazaporphin. The tetrabenzotriazaporphin prepared by this method is present in the α-modification, which shows strong bands in the X-ray diffraction photograph at the Bragg angles 6.7; 13.6; 15.0; 24.5 and 26.9.

This process for the preparation of compounds of the formula (IV) is very lengthy, since first the methylenephthalimidinoacetic acid has to be prepared in a two-step synthesis. Moreover the metal-free tetrabenzotriazaporphin can only be obtained via the magnesium complex by dissolution and reprecipitation from sulphuric acid, which results in an expensive work-up or disposal of the sulphuric acid solution.

A further process for the preparation of tetrabenzotriazaporphin is described by Barrett, Linstaed and Tuey (J. Chem. Soc. 1939, p. 1809–1822) by reaction of phthalodinitrile with methylmagnesium iodide or methyllithium in ether.

The tetrabenzotriazaporphin prepared by this method is present in the β-modification, which shows strong bands in the X-ray diffraction photograph at the Bragg angles 7.0; 8.9; 17.9; 20.3; 23.7; 26.0; 26.8; 27.7 and 30.0.

A disadvantage of this process is the use of ether as solvent. Because of the low ignition point and the tendency to form explosive peroxides, the use of ether in industry as solvent is subject to stringent safety regulations. Moreover organometallic reagents, such as methyllithium and methylmagnesium iodide, due to their very high reactivity and the tendency to develop explosive gases upon contact with moisture, are expensive and can only be reacted in special equipment.

In contrast, the process according to the invention starts with readily available starting materials, and the products of the general formula (IV) can be prepared directly in a one-step synthesis in metal-free form.

Heating (I) where n is O and R is H or acyl with (V) where n is O and R is H or acyl in a molar ratio of about 1:1 gives the tetrabenzotriazaporphin

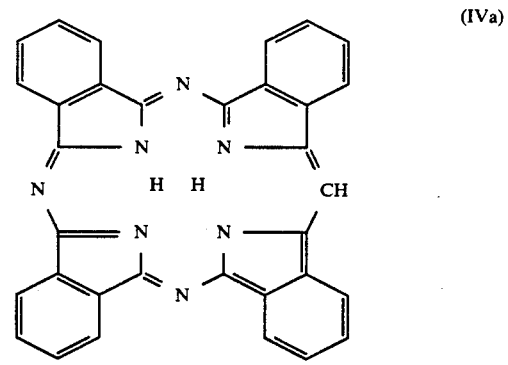

(IVa)

in the known β-modification.

Grinding the β-modification of the compound of the formula (IVa), if appropriate in the presence of an inorganic or organic salt, gives the new ω-modification of the compound of the formula (IVa), which in the X-ray diffraction photograph shows strong bands at the Bragg angles 8.5; 10.2; 11.9; 14.4; 18.0; 20.4; 22.6; 24.0; 24.7 and 29.8 and to which the invention also relates.

The grinding is preferably carried out in the presence of salts, in particular inorganic salts, for example the alkali metal salts of strong inorganic acids, such as NaCl, preferably at room temperature.

A further process for the preparation of the ω-modification of the compound of the formula (IVa) consists in heating the α-modification of the compound of the formula (IVa) by heating to 100° to 300° C., preferably in the presence of a solvent.

Suitable solvents are organic solvents, for example alcohols, phenols, dipolar aprotic solvents, such as dimethylformamide, dimethylacetamide, dimethyl sulphoxide, N-methylpyrrolidone, and preferably aliphatic or aromatic hydrocarbons, which can be unsubstituted or substituted by alkyl, acyl, alkoxy, halogen, ester or nitro groups, such as decalin, xylene, metsitylene, chlorobenzene, dichlorobenzene, trichlorobenzene, naphthalene, 1-methylnaphthalene, methyl benzoate, 2-methylnaphthalene, 1-chloronaphthalene, 2-chloronaphthalene and unsubstituted or substituted heterocyclic solvents, such as pyridine, picoline, quinoline.

A further process for the preparation of the ω-modification of the compound of the formula (IVa) consists in carrying out the synthesis of the pigment by the preparation process according to the invention in the presence of preferably 0.001 to 0.1 mole of the ω-modification of the compound of the formula (IVa), relative to 1 mole of the compound of the formula (I).

The ω-modification of the compound of the formula (IVa) is usable for a wide range of the abovementioned pigment applications and as an organic photoconductor pigment, due to its particularly good pigment properties.

EXAMPLE 1

72.5 g of aminoiminoisoindolenine and 81 ml of nitromethane are refluxed in 400 ml of methanol for 12 hours. The crystals formed are filtered off with suction while cold and washed with methanol to give 62 g of a compound which in one of its tautomeric forms has the formula

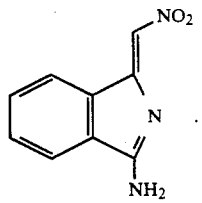

EXAMPLE b 2

The procedure of Example 1 is repeated, except that a weak air flow is passed through the solution during the reaction. Yield: 68 g of the compound obtained in Example 1.

EXAMPLE 3

The procedure of Example 1 is repeated, except that 87.5 g of 5-methoxyaminoiminoisoindolenine are used instead of the aminoiminoisoinodolenine to give 63 g of a compound which in one of its tautomeric forms has the formula

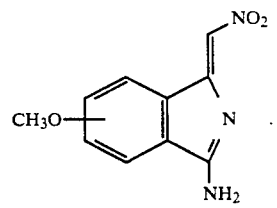

EXAMPLE 4

The procedure of Example 1 is repeated, except that 97.5 g of benzoaminoiminoisoindolenine are used instead of the aminoiminoisoindolenine, to give 94.4 g of a compound which in one of its tautomeric forms has the formula

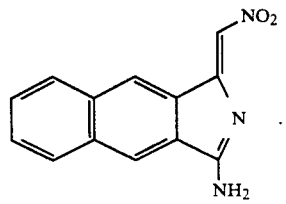

EXAMPLE 5

500 ml of 1-methylnaphthalene are heated in a distillation apparatus to 240° C. Over a period of 30 minutes, a suspension of 189 g of the compound from Example 1 and 145 g of aminoiminoisoindolenine in 700 ml of 1-methylnaphthalene are added dropwise, while the water of reaction is continuously distilled off. The mixture is then stirred for 10 hours at 240° C., the crystals formed are filtered off with suction while cold and thoroughly washed with DMF and methanol to give 102 g of the compound of the formula

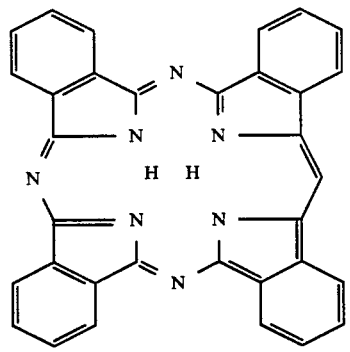

in the β-modification.

EXAMPLE 6

71 g of the compound from Example 1, 55 g of aminoiminoisoindolenine and 500 ml of nitrobenzene are refluxed for 3 hours. The product is filtered off with suction while cold and thoroughly washed with DMF and methanol to give 31.2 g of the compound from Example 5 in the β-modification.

EXAMPLE 7

21.9 g of the compound from Example 3 and 14.5 g of aminoiminoisoindolenine are refluxed in 100 ml of o- dichlorobenzene for 12 hours. The product is filtered off with suction while cold and washed with methanol to give 13.2 g of the compound of the formula

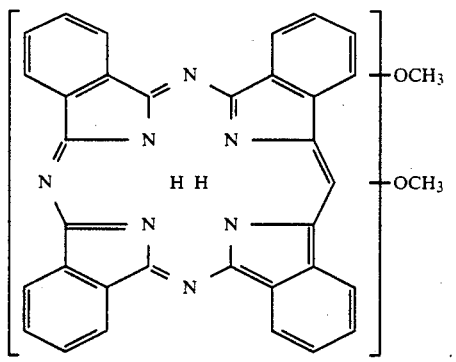

EXAMPLE 8

28.4 g of the compound from Example 1 and 26.3 g of 5-methoxyaminoiminoisoindolenine are refluxed in 100 ml of xylene for 24 hours. The crystals are filtered off with suction, stirred in DMF and washed with methanol to give 21.3 g of the compound from Example 7.

EXAMPLE 9

56.7 g of the compound from Example 1 are refluxed in 250 ml of amyl alcohol for 12 hours. The crystals are filtered off with suction while cold and washed with DMF and ethanol to give 5.3 g of a mixture of the compound from Example 5, tetrabenzodiazaporphin and tetrabenzomonoazaporphin.

EXAMPLE 10

38.7 g of the compound from Example 1 and 14.5 g of aminoiminoisoindolenine are refluxed in 100 ml of chloronaphthalene for 2 hours. The crystals obtained are filtered off with suction and washed with acetone to give 9.3 g of a mixture of the compound from Example 5 and tetrabenzodiazaporphin.

EXAMPLE 11

18.9 g of the compound from Example 1 and 43.5 g of aminoiminoisoindolenine are refluxed in 100 ml of nitrobenzene for 12 hours. The product is filtered off with suction while cold to give 16.4 g of a mixture of phthalocyanine and the compound from Example 5.

EXAMPLE 12 (USE EXAMPLE)

4 g of finely ground pigment according to Example 5 are dispersed in 92 g of a stoving enamel of the following composition:
33% of alkyd resin
15% of melamine resin
5% of glycol monomethyl ether
34% of xylene
13% of butanol Suitable alkyd resins are products based on synthetic and vegetable fatty acids, such as coconut oil, castor oil, ricinene oil, linseed oil and the like. Instead of melamine resins, urea resins can be used.

After the dispersion is complete the pigmented lacquer is applied to paper, glass, plastic or metal sheets and stoved at 130° C. for 30 minutes to give a green coating.

EXAMPLE 13 (USE EXAMPLE)

0.2 g of the pigment obtained by Example 5 is dispersed at 160° C. on mixing rolls in 65 g of stabilized PVC and 35 g of diisooctyl phthalate and rolled at 160° C. to give a green sheet of very good light and migration fastness.

EXAMPLE 14

10 g of tetrabenzotriazaporphin in the β-modification, prepared, for example, by Example 5, 90 g of common salt and 600 g of steel beads are milled in a vibrating mill for 10 hours, then stirred in hot water and washed until salt-free to give 9.9 g of tetrabenzotriazaporphin in the new ω-modification.

EXAMPLE 15

9 g of tetrabenzotriazaporphin from Example 14 are stirred in 100 ml of methyl benzoate at 150° C. for 10 hours. The product is filtered off with suction when cold, washed with methanol and dried to give 8.8 g of tetrabenzotriazaporphin in the ω-modification, which exhibit an increased hiding power in the coating.

EXAMPLE 16

10 g of tetrabenzotriazaporphin of any desired modification are dissolved in 100 g of concentrated sulphuric acid, and the solution is poured into 900 ml of water over a period of 30 minutes. The product which precipitates in finely divided form is filtered off with suction, washed with water until sulphate-free and dried at 50° C. in a circulating air drying cabinet to give 9.5 g of tetrabenzotriazaporphin in the α-modification.

EXAMPLE 17

9.5 g of tetrabenzotriazaporphin in the α-modification, prepared by Example 16, are suspended in 100 ml of methyl benzoate and stirred at 180° C. for 10 hours. The product is filtered off with suction while cold, thoroughly washed with methanol and dried to give 9 g of tetrabenzotriazaporphin in the ω-modification.

EXAMPLE 18

The procedure of Example 5 is repeated, except that 5 g of the compound from Example 14 are added as seed crystals, to give 110 g of tetrabenzotriazaporphin in the ω-modification.

EXAMPLE 19 (USE EXAMPLE)

4 g of finely ground pigment according to Example 14 are dispersed in 92 g of a stoving enamel of the following composition:
33% of alkyd resin
15% of melamine resin
5% of glycol monomethyl ether
34% of xylene
13% of butanol Suitable alkyd resins are products based on synthetic and vegetable fatty acids, such as coconut oil, castor oil, ricinene oil, linseed oil and the like. Instead of melamine resins, urea resins can be used.

After the dispersion is complete the pigmented lacquer is applied to paper, glass, plastic or metal sheets and stoved at 130° C. for 30 minutes to give a green coating.

EXAMPLE 20 (USE EXAMPLE)

6 parts of the pigment according to Example 14 are dispersed in 12 parts of xylene, 4.1 parts of butyl acetate and 0.7 part of n-butanol with 22.5 parts of a 20 % strength solution of cellulose acetobutyrate in butyl acetate/xylene (2:1) in the Red Devil together with glass beads of 2 to 3 mm for 30 minutes. After fattening up by adding 10 parts of a saturated polyester resin (Dynapol H 700), 7.3 parts of melamine resin, 8.7 parts of a 20% strength solution of cellulose acetobutyrate in butyl acetate/xylene (2:1), 18 parts of butyl acetate, 1.6 parts of n-butanol and 9.7 parts of xylene, the mixture is dispersed for another 5 minutes.

A dispersion of an aluminium paste (60%) in an organic solvent (about 1:2) is added to this paint in such an amount that the ratio of pigment:Al is between 80:20 and 1:99.

This paint is applied and, after drying, it is coated with a clear coat based on acrylate/melamine resin, which can contain further auxiliaries, such as, for example, UV absorbers, and stoved.

A green metallic coating having excellent weather fastness is obtained.

EXAMPLE 21

0.2 g of the pigment obtained according to Example 14 is dispersed at 160° C. on mixing rolls in 65 g of stabilized PVC and 35 g of diisooctyl phthalate and rolled at 160° C. to give a green sheet of very good light and migration fastness.

We claim:

1. A process for the preparation of prophyrins or mixtures of porphyrins of the formula

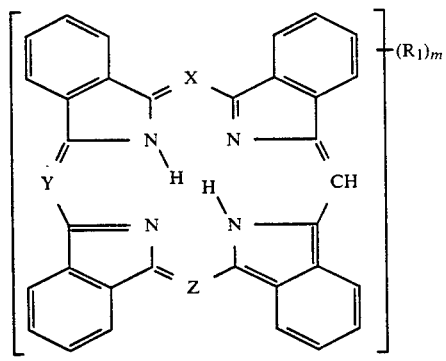

in which
X, Y, Z independently of one another, are CH or N, but at least one of X, Y or Z represents N,
$R_1$ has the meaning given below and
m is 0 to 8,
characterized in that a compound of the formula

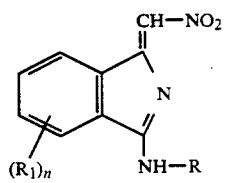

wherein
R denotes hydrogen, acetyl or benzoyl,
$R_1$ denotes hydrogen, $C_1$–$C_6$-alkyl, phenyl, biphenyl, naphthyl, a heterocyclic aromatic radical containing 1 or 2 five-, six- or seven-membered rings, at least one of which contains 1, 2 or 3 heteroatoms from the series comprising O, N, S or denotes $C_1$–$C_4$-alkylcarbonyl or substituted or unsubstituted phenylcarbonyl, $C_1$–$C_6$-alkoxy, halogen, carboxyl, carboxamido, cyano or nitro, or two adjacent substituents $R_1$ can form a benzene ring together with the C-atoms on the benzene ring linking them,
and it being possible for the phenyl, biphenyl, naphthyl radicals, the heterocyclic aromatic radicals and the benzene ring mentioned above to contain substituents from the series comprising F, Cl, Br, $C_1$–$C_6$-alkyl, $C_1$–$C_6$-alkoxy, unsubstituted amino, carboxyl, carboxamido, sulpho, sulphonamido, $C_1$–$C_6$-alkoxycarbonyl, sulphonylamino, $C_1$–$C_6$-alkylsulphonyl, $C_1$–$C_4$-alkylcarbonyl, phenylcarbonyl or aminocarbonyloxy and
n denotes 0 to 2
is heated to temperatures of about 100°–300° C.

2. A process for the preparation of porphyrins or mixtures of porphyrins of the formula

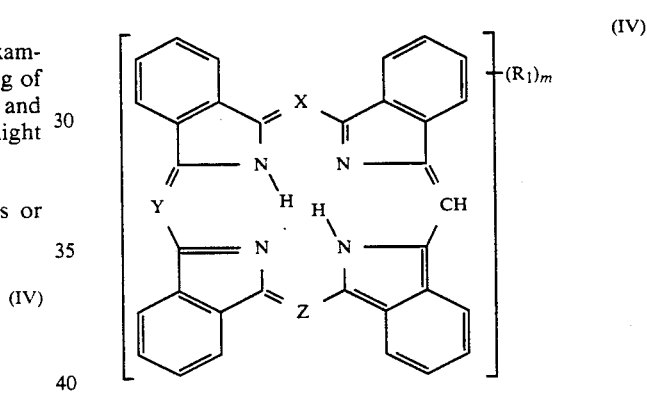

in which
X, Y, Z, independently of one another, are CH or N, but at least one X, Y or Z represents N,
$R_1$ has the meaning given below and
m is 0 to 8,
characterized in that a compound of the formula

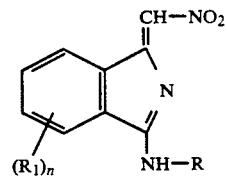

wherein
R denotes hydrogen, $C_1$–$C_6$-alkyl, phenyl, biphenyl, naphthyl, a heterocyclic aromatic radical containing 1 or 2 five-, six- or seven-membered rings, at least one of which contains 1, 2 or 3 heteroatoms from the series comprising O, N, S or denotes $C_1$–$C_4$-alkylcarbonyl or substituted or unsubstituted phenylcarbonyl,
and it being possible for the phenyl, biphenyl, and naphthyl radicals and for the heterocyclic aromatic radical mentioned above to contain substituents from the series comprising F, Cl, Br, $C_1$–$C_6$-alkyl, $C_1$-$C_6$-alkoxy, unsubstituted amino, carboxyl, carboxamido, sulpho, sulphonamido, $C_1$-$C_6$-alkoxycarbonyl, sulphonylamino, $C_1$-$C_6$-alkylsulphonyl, $C_1$-$C_4$-alkylcarbonyl, phenylcarbonyl or aminocarbonyloxy and $R_1$ and n have the meaning given in claim 1 is heated in a mixture with an effective amount of up to 20 mol of a compound

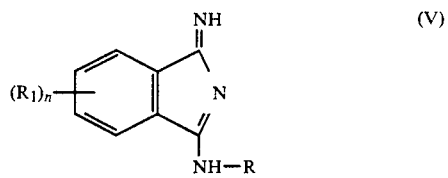

in which $R_1$ and n have the meaning given in claim 1 to temperatures of about 100°–300° C.

3. A process according to claim 1, wherein the reaction mixture is heated to a temperature of about 150°–270° C.

4. A process according to claim 2, wherein the reaction mixture is heated to a temperature of about 150°–270° C.

* * * * *